US010820988B2

United States Patent
Scorsin et al.

(12) United States Patent
(10) Patent No.: US 10,820,988 B2
(45) Date of Patent: Nov. 3, 2020

(54) EXPANDABLE STENT-VALVE AND METHOD FOR MANUFACTURING A STENT

(71) Applicant: EPYGON, Paris (FR)

(72) Inventors: Marcio Scorsin, Curitiba (BR); Enrico Pasquino, Marentino (IT)

(73) Assignee: EPYGON, Paris (FR)

( * ) Notice: Subject to any disclaimer, the term of this patent is extended or adjusted under 35 U.S.C. 154(b) by 0 days.

(21) Appl. No.: 14/783,666

(22) PCT Filed: Apr. 8, 2014

(86) PCT No.: PCT/EP2014/057031
§ 371 (c)(1),
(2) Date: Oct. 9, 2015

(87) PCT Pub. No.: WO2014/166939
PCT Pub. Date: Oct. 16, 2014

(65) Prior Publication Data
US 2016/0302919 A1 Oct. 20, 2016

(30) Foreign Application Priority Data
Apr. 9, 2013 (EP) .................................... 13305461

(51) Int. Cl.
*A61F 2/24* (2006.01)
*A61F 2/00* (2006.01)
(Continued)

(52) U.S. Cl.
CPC .......... *A61F 2/2418* (2013.01); *A61F 2/0077* (2013.01); *A61F 2/2412* (2013.01);
(Continued)

(58) Field of Classification Search
CPC .. A61F 2/2418; A61F 2/04; A61F 2/06; A61F 2/07; A61F 2/82; A61F 2/0077;
(Continued)

(56) References Cited

U.S. PATENT DOCUMENTS

2004/0098101 A1 5/2004 Kuribayashi et al.
2006/0287719 A1* 12/2006 Rowe .................... A61F 2/2409 623/2.18

(Continued)

FOREIGN PATENT DOCUMENTS

EP 0850604 A2 7/1998
EP 1893132 A2 11/2006

(Continued)

OTHER PUBLICATIONS

International Search Report for PCT/EP2014/057031, dated Jul. 22, 2014, 4 pages.

(Continued)

*Primary Examiner* — Dinah Baria
(74) *Attorney, Agent, or Firm* — Nixon & Vanderhye P.C.

(57) ABSTRACT

An expandable stent-valve has a stent component and a valve component, preferably an aortic valve component, a mitral valve component or a tricuspid valve component. The stent has, an outer surface area structured in a manner such that the surface area has a higher coefficient of friction between the outer surface and a duct wall than an untreated surface area of the stent component. The surface area is preferably structured with micro-incisions or micro-grooves.

6 Claims, 5 Drawing Sheets

Figure 1A:
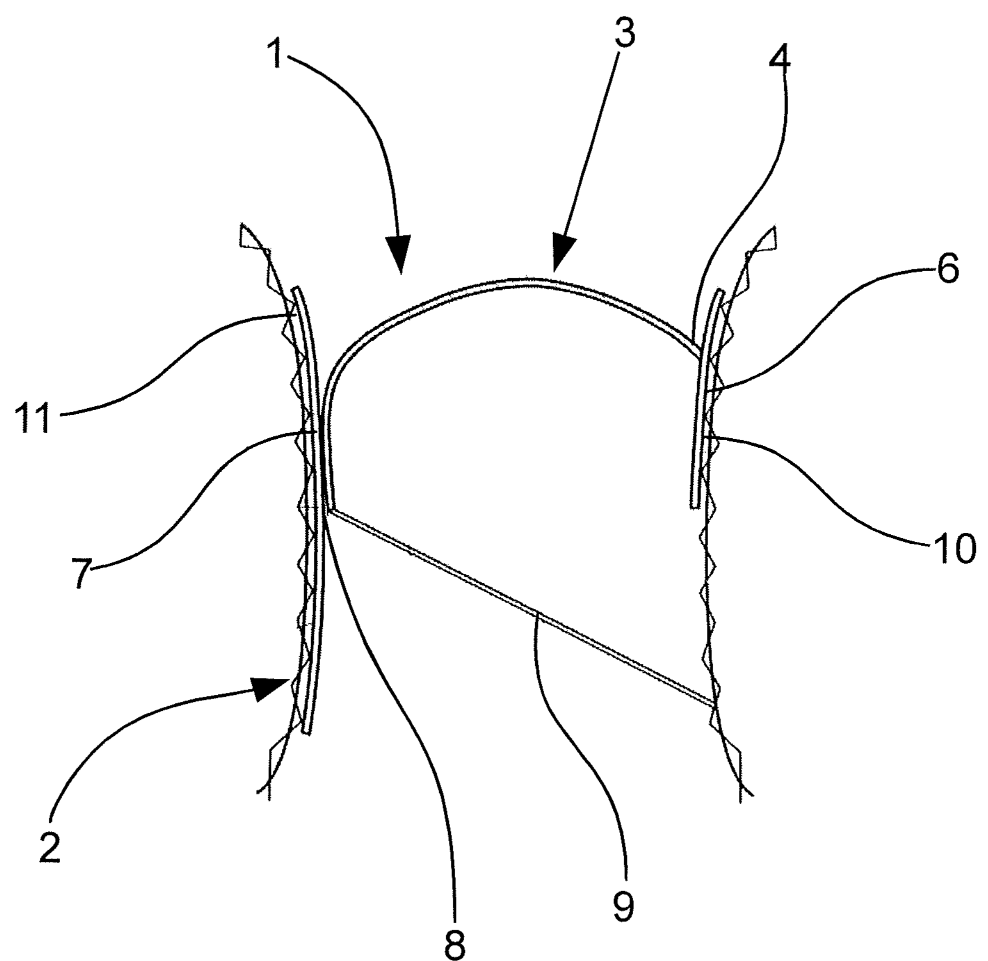

(51) Int. Cl.

*A61F 2/844* (2013.01)
*A61F 2/848* (2013.01)
*A61F 2/82* (2013.01)
*A61F 2/04* (2013.01)

(52) U.S. Cl.

CPC .............. *A61F 2/844* (2013.01); *A61F 2/848* (2013.01); *A61F 2/04* (2013.01); *A61F 2/82* (2013.01); *A61F 2002/0081* (2013.01); *A61F 2220/0008* (2013.01); *A61F 2230/0006* (2013.01); *A61F 2230/0023* (2013.01); *A61F 2230/0054* (2013.01); *A61F 2230/0056* (2013.01); *A61F 2230/0058* (2013.01); *A61F 2250/0014* (2013.01); *A61F 2250/0021* (2013.01); *A61F 2250/0026* (2013.01); *A61F 2250/0036* (2013.01)

(58) Field of Classification Search

CPC .... A61F 2/848; A61F 2/91; A61F 2230/0054; A61F 2230/0056; A61F 2230/0058; A61F 2250/0021; A61F 2250/0026; A61F 2002/0081

See application file for complete search history.

(56) References Cited

U.S. PATENT DOCUMENTS

2008/0183276 A1* 7/2008 Melder ................... A61L 27/28 623/1.15
2009/0132035 A1 5/2009 Roth et al.
2010/0331972 A1 12/2010 Pintor et al.
2011/0276125 A1* 11/2011 Walker .................... A61F 2/915 623/1.15
2011/0288632 A1 11/2011 White
2012/0035715 A1 2/2012 Robida et al.
2012/0282391 A1 11/2012 Palmaz et al.
2012/0310328 A1 12/2012 Olson et al.
2014/0114435 A1* 4/2014 Carpenter ............. A61F 2/0077 623/23.76
2019/0201184 A1 7/2019 Treacy et al.

FOREIGN PATENT DOCUMENTS

WO 98/55047 A1 12/1998
WO 2008/028569 A1 3/2008
WO 2009/106545 A1 9/2009
WO 2012/063228 A1 5/2012

OTHER PUBLICATIONS

Written Opinion of the ISA for PCT/EP2014/057031, dated Jul. 22, 2014, 7 pages.

Communication pursuant to Article 94(3) EPC dated Oct. 17, 2016, issued in European Patent Application No. 14 715 629.3.

Communication pursuant to Article 94(3) EPC dated Feb. 10, 2017, issued in European Patent Application No. 14 715 629.3.

Choy, Jenny Susana, et al., "Scaling of Myocaridal Mass to Flow and Morphometry of Coronary Arteries," J Appl Physiol, May 2008, vol. 104, No. 5, pp. 1281-1286.

Dodge, J. Theodore, Jr., et al., "Lumen Diameter of Normal Human Coronary Arteries—Influenece of Age, Sex, Anatomic Variation, and Left Ventricular Hypertrophy or Dilation," Circulation, vol. 86, No. 1, Jul. 1992, pp. 232-246.

Menger, M. D., et al., "Quantitative analysis of neovascularization of different PTFE-implants," European Journal of Cardio-thoracic Surgery, 1990, vol. 4, pp. 191-196.

Rieger, Elisabeth, et al., "Controlled implant/soft tissue interaction by nanoscale surface modifications of 3D porous titanium implants," The Royal Society of Chemistry, Nanoscale Accepted Manuscript, 2015, 33 pages.

Communication pursuant to Article 94(3) EPC dated Apr. 3, 2017, issued in European Application No. 14715629.3, 5 pages.

* cited by examiner

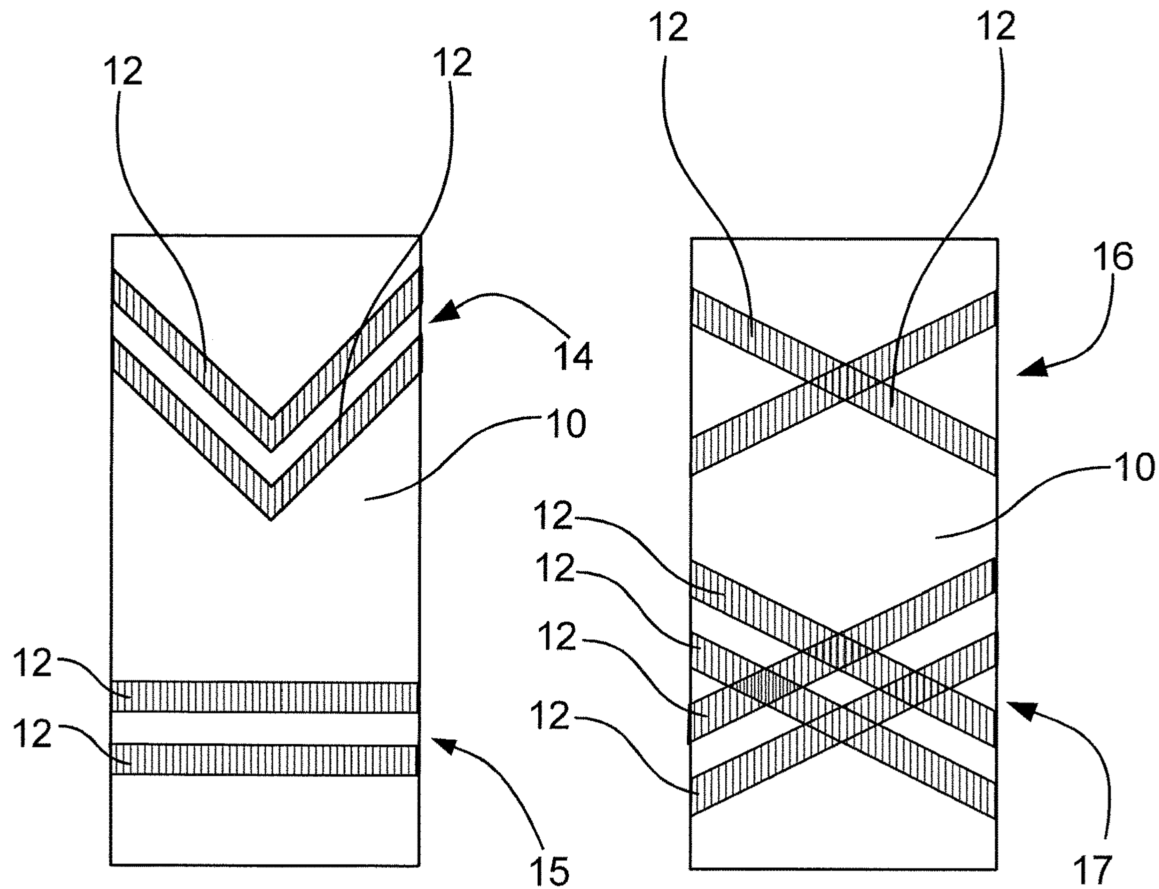
Fig. 4a
Fig. 4b
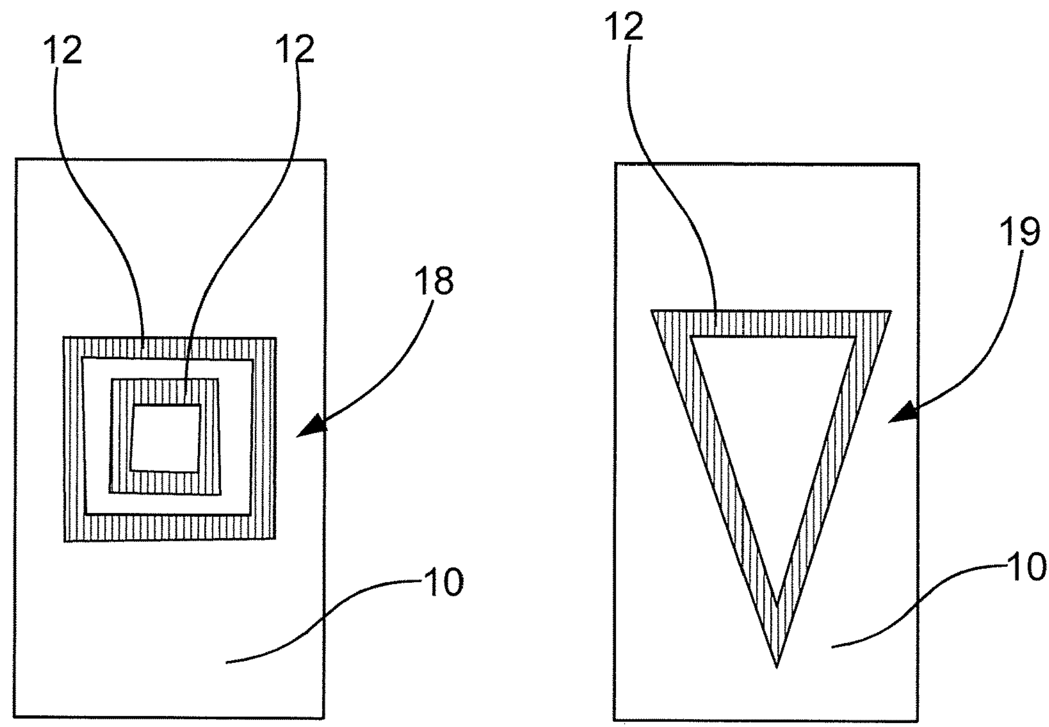
Fig. 4c
Fig. 4d

EXPANDABLE STENT-VALVE AND METHOD FOR MANUFACTURING A STENT

This application is the U.S. national phase of International Application No. PCT/EP2014/057031 filed Apr. 8, 2014, which designated the U.S. and claims priority to EP Patent Application No. 13305461.9 filed Apr. 9, 2013, the entire contents of each of which are hereby incorporated by reference.

The invention is directed to stents and to methods for producing the stents.

The replacement of cardiac valves with prostheses is a complex operation, often carried out by an open heart surgery. The operation requires the opening of the chest, as well as the arrest of the patient's heart. During the last years, minimal invasive systems have been established to percutaneously deliver a stent prosthesis by a catheter.

Upon arriving at an implantation site, the stent is released from the catheter and expands either by self-expanding or with the aid of auxiliary means such as balloons. After the stent is expanded, the stent has to be anchored at the implantation site for a reliable functioning. Different ways of anchoring have been proposed, such as suturing the stent to the tissue or anchoring the stent with hooks or barbs. These techniques have the disadvantage of piercing and thus injuring a surrounding tissue. Further, reliable anchoring is difficult to achieve with these known products. Especially in mitral valves, where pressure differences are even bigger than in other heart valves, a secure anchoring is required.

WO 2009/106545 further suggests using stents having finger like elements providing a radially acting tension force on the vascular wall. The tension force of the finger like elements anchors the stent.

Another possibility to anchor stents, is outer shape permitting a form fit anchoring at the native anatomy. EP 1 893 132 suggests a stent with an asymmetrical hour-glass shape, wherein the portion with the larger diameter provides an anchoring of the stent through form fit. WO 2008/028569 suggest providing a round orifice for securing the stent valve through form fit.

WO 2012/063228 proposes a solution with a support structure and an anchoring member. The anchoring member is separate from the support structure and comprises for example a ring. The anchoring member co-operates with the peripheral wall of the support structure, extending around it so as to lock the valve leaflets of the cardiovascular valve between the anchoring member and the peripheral wall of the support structure.

However, such a construction is complicated as there are two separate members which have to be connected inside the body. The combination has to be very accurate to provide a reliable anchoring.

Hence, there is a need for stents which avoid the disadvantage of the known state of the art. In particular, there is a need for stents which provide a reliable anchoring system with a simple and efficient construction and which are easy to use.

The present invention provides an expandable stent-valve having a stent component and a valve component. Preferably the valve component is an aortic valve component, a mitral valve component, a tricuspid valve component or a pulmonary valve component. The stent component comprises an outer surface area structured in a manner such that the surface area has a higher coefficient of friction between the outer surface and a duct wall than an untreated surface area of the stent component. The surface area is preferably structured with micro-incisions or micro-grooves.

The stent might be formed out of struts in a range of 0.2 mm to 0.8 mm. The depth of the incisions can be estimated in a range from 10% to 70% of the depth of the strut. The struts' width is also in a range from 0.2 mm to 0.8 mm and the incisions have about the same width as depth. The dimensions of the incisions are related to stent design, incision design and the technique adopted to produce the incision. Therefore, an incision parallel to the length of the strut can be longer than incisions perpendicular or diagonal to the length of the strut.

The coefficient of friction (COF) is a dimensionless scalar value which describes the ratio of the force of friction between two bodies and the force pressing them together. The force of friction is dependent on the material itself, as well as on the surface texture. In context with the present application structuring or texturing to increase the coefficient of friction can be on a microscopic level but also—and preferably—on a macroscopic level.

The structures turn a regular surface area into an irregular one. An irregular surface area is to be understood as comprising structures which either protrude from or intrude into the surface. With an embodiment comprising an irregular structure the force necessary to move the stent in its deployed state within a duct, is bigger than the force required to move a stent with a regular surface. The increased COF prevents the stent-valve from undesired movements like e.g. slippage or rotation, once deployed at an implantation site.

An anchoring of a stent with an increased COF according to the invention is especially desired in ducts with high pressure settings and/or a tendency for chronic dilation/enlargement such as an aorta, pulmonary artery or the left or right atrium.

However, the stents according to the invention could also be used in blood vessels to e.g. treat aneurysm or stenosis. These stents are constructed in a similar way than the stent-valves for the cardiac valves but lack a valve component.

In a preferred embodiment the outer surface area is structured in a manner such that some structures, preferably all structures, are designed such as to allow ingrowth of a tissue into the outer surface.

Intrusions like e.g micro-incisions or micro-grooves have been shown to be especially advantageous for tissue ingrowth. Cells of the surrounding tissue can grow into the intrusions, whereby very thin intrusions promote cell-ingrowth. In addition to the increased COF, the ingrowed tissue provides a further anchoring. Especially in view of long term anchoring, tissue ingrowth is desirable as the stent is securely fixed in the tissue.

It is also possible to provide the outer surface with protrusions, wherein the tissue can grow into the cavities between the protrusions. Protrusions should be arranged at small distances to each other to achieve thin cavities which promote the cell-ingrowth.

The outer surface area might also be structured in a manner that some structures, preferably all structures, are designed as orifices passing through from the outer surface to an inner surface. The orifices can be designed as circular holes or as elongated slits.

The orifices allow the tissue of the duct wall to reach a deep tissue colonization to further anchor the structure. The tissue might grow inside a lumen of the stent. Ingrown tissue from two or more orifices might then merge and thus provide a secure long term anchoring of the stent.

The pass through orifices might have a varying diameter along their axis. Diverging orifices or orifices which have a stepped form in a longitudinal section are possible. It is also possible to provide orifices with a constant diameter.

It is of course possible that pass through orifices are combined with other COF enhancing structures on the outer surface. A combination of pass through orifices and non pass through incisions or with protrusions is possible.

It is also possible to provide the structures (intrusions, protrusions, walls of pass through orifices) with a drug promoting cell growth. By chemically promoting cell growth a long term anchoring is achieved even faster.

In a further preferred embodiment, the structures are designed in a manner that a kind of suction between the treated outer surface area and the duct wall can occur. The suction is similar to a sort of vacuum effect comparable to e.g. a suction cup.

The force of pressing the stent and the duct wall together is enhanced through the suction. As the friction force is directly proportional to the force of pressing the surfaces together, the friction force is also enhanced as a result.

Again, intrusions, like micro-incisions or micro-grooves have shown to exhibit a good suction. Although other structures are possible, micro-intrusions are preferred.

With a structure which provides suction and enhances the COF, the anchoring of the stent is improved, as the variables defining the friction (COF, force of pressing together) are enhanced.

The whole outer surface of the stent can be structured, whereas the inner surface typically remains unstructured. By providing the structure on the whole outer surface, it is guaranteed, that the surrounding tissue is in contact with the structures. Ducts in different patients are not identical. With a stent having the whole outer surface area treated, the outer surface is always in contact with the duct wall irrespective of the specific anatomy.

In an alternative embodiment, the treated surface area is arranged at least in and preferably only in a region intended to get in contact with the tissue of the duct, e.g. in a region exposed to most exposition/enlargement.

The duct wall at the implementation site might not be homogenously exposed to exposition/enlargement. Movements of the stent are often occurring, if the stent is not properly anchored in the regions exposed to most exposition/enlargement. A structured outer surface according to the invention in the areas in contact with the most exposed area of the duct wall might therefore be sufficient to securely anchor the stent. However, to guarantee a secure anchoring in different patients, treatment of the whole outer surface is preferred.

The structures of the outer surface area might have a V-form and/or double V-form and/or X-form and/or line-form and/or double X-form or a rectangular-form and/or a double rectangular-form and/or a triangle-form and/or a double-triangle-form.

These forms have shown to provide a reliable increase in COF. Further tissue ingrowth is possible with these structures, if provided in the suitable dimensions. As micro-incisions and micro-grooves have shown to suit the purpose perfectly, the forms are preferably produced in small dimensions. It is possible to provide an outer surface with structures of different shapes.

The listed shapes are just a selection of possible shapes and are not to be seen as exhaustive. The outer surface might also have structures in annular-form or zig-zag-form, etc.

The structures of the outer surface are preferably obtainable by laser cutting and/or chemical hatching and/or mechanical tooling.

Often stents are produced by laser cutting the outline of the stents in a tube or plate of metal, such as nitinol or other biocompatible materials. By providing also the structures with laser cutting, the structures can be produced in the same operational step.

But also chemical hatching and mechanical tooling have shown to provide suitable structures. The used method depends on the material used for the stent and on the shape of the structure.

The structures might be produced by either technique either before the stent is laser cut or after the stent is laser cut out of a metal tube. In the latter case, the structures might be produced before or after expanding of the stent. Applying the structures to the uncut stent has the advantage of that the structures can easily be positioned avoiding intersection with critical structural parts of the stent and therefore preserving the mechanical and fatigue resistance of the stent.

Laser cutting allows the creation of structures in flat metal sheets with high depths (up to 20 mm). Laser cutting further allows the production of very precise structures.

In metal sheets with a thickness of not more than 6 mm, the creation of structures can also be achieved through punching which basically means the pressing down of a flat metal surface.

The stent is typically formed as a tubular structure comprising a plurality of struts arranged in a substantially axial or circumferential manner. Typically the outer surface of these struts is provided with the structure according to the invention.

The invention further provides a method for manufacturing a stent providing a preform stent, comprising the steps of treating an outer surface area preferably treating an outer surface area by providing micro-incisions or micro grooves on the outer surface.

The method can be used for any stents, including cardiac stents but also stents used in blood vessels to e.g. treat aneurysm or stenosis.

To provide cardiac stent valves, the method comprises the further step of assembling a valve component to the stent.

Preferred valves are the mitral valve, the aortic valve, the tricuspid valve and the pulmonary valve. The valve can be assembled to the stent in different ways known in the state of the art, e.g. suturing.

In a preferred method the outer surface is treated with laser cutting.

In a preferred method to produce stent-valves the outer surface is treated with laser cutting and/or chemical hatching and/or mechanical tooling to obtain the treated outer surface.

Further preferred is a method, wherein the outer surface is treated such as to provide structures in a V-form and/or double V-form and/or X-form and/or line-form and/or double X-form or a rectangular-form or a double rectangular-form and/or a triangle-form or a circular-form or double circular-form.

In a preferred method, the whole outer surface of the stent is treated.

Alternatively, only a part of the outer surface area is treated. It is for example possible to provide a method, wherein only the outer surface area is treated which is intended to get in contact with the duct wall area exposed to most dilation/enlargement.

A further aspect of the invention is a delivery device comprising a stent as described above.

The delivery device is preferably a catheter device able to accept the stent in a crimped form. With the delivery device, the stent can be delivered to the implementation site. After release from the delivery device, the stent expands and can fulfil its function as cardiac valve prosthesis.

The invention further provides a method to treat stenosis or aortic aneurysm or a defective valve, preferably a mitral valve or an aortic valve or a tricuspid valve or a pulmonary valve. The method comprises the steps of:

delivering a stent, preferably a stent as described above, with a delivery device, preferably a delivery device as described above, releasing the stent from the delivery device at the anatomical target, such that the stent expands, wherein the stent frictionally anchors in a duct with the help of at least one treated surface area on an outer surface of the stent. Preferably, the whole outer surface is treated.

Further aspects of the invention are described relating to the figures. The figures show schematically:

FIG. 1*a*: A longitudinal section through a mitral stent-valve

Figure 1B:
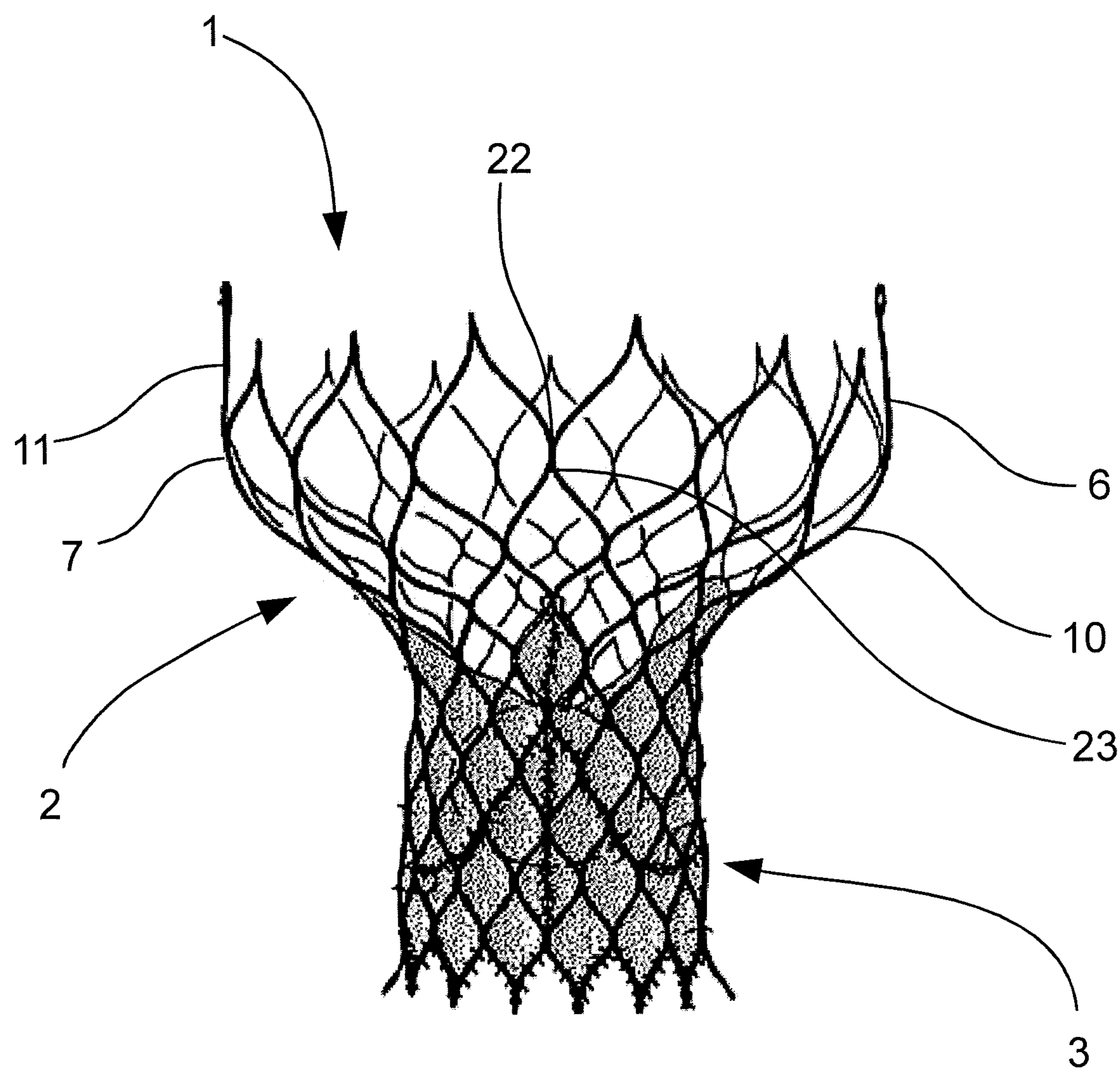

FIG. 1*b*: An aortic stent-valve

Figure 2:
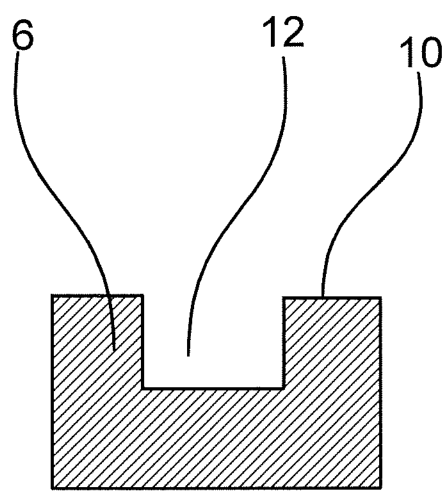

FIG. 2: A Cross section of a wall portion of a stent according to the invention FIG. 3: A Cross section of a wall portion of a stent according to an alternative embodiment FIG. 4*a-d*: Different forms of micro incisions on outer surfaces FIG. 5: A detailed view of structured wall portions FIG. 1*a* shows a longitudinal section through a mitral stent-valve 1. The stent-valve comprises a generally tubular stent component 2 made of Nitinol through laser-cutting and a valve component 3. The valve component 3 is connected to the stent component. A root end 4 of the valve component 4 is connected to a support wall portion 6 of the stent component. Opposite the support wall portion 6 there is a complementary wall portion 7.

The complementary wall portion 7 supports a static or quasi-static coaptation surface 8 adapted to be sealingly engaged by a free end 5 of the valve component 3. The free end 5 of the valve component 3 is connected to the support wall portion 6 of to the complementary wall portion 7 by with a traction member 9. The traction member 9 is made out of a flexible material and dimensioned to such a length that the movement of the free end 5 of the valve component 3 is stopped at the coaption surface 8. The support wall portion and the complementary wall portion are part of the generally tubular stent and each have an outer surface 10, 11. The outer surfaces 10, 11 are structured with micro-incisions (not shown in FIG. 1, see. e.g. FIG. 2). The micro-incisions increase the coefficient of friction between a duct wall and the stent-valve when implanted. Other parts of the stent in contact with surrounding tissue may also be structured.

FIG. 1*b* shows an aortic stent-valve 1. The stent valve comprises a tubular generally tubular stent-component 2 having a hour-glass shape. The stent component 2 is made of Nitinol through laser cutting. The aortic stent valve 1 further comprises a valve component 3 which is sutured to the stent component 2. The stent comprises a support wall portion 6 and a complementary wall portion 7 with outer surfaces 10, 11. It has to be understood that in the aortic stent-valve 1 as well as in the mitral stent-valve, support wall portion 6 and complementary wall portion 7 are only referred to as separate elements for a better understanding. As seen in FIG. 1*b*, the stent-valve is generally tubular and comprises wall portions 22 all around. All wall portions 22 are provided with micro-incisions on their outer surfaces 23.

FIG. 2 shows a cross section of a strut like element forming the support wall 6. The outer surface 10 is provided with micro-incisions 12. The micro-incision is provided by laser-cutting. The micro-incisions 6 are arranged on the whole outer surface 10 of the support wall. The micro-incision 12 is constructed as to allow tissue ingrowth. Although FIG. 2 only shows the support wall 6, it is to be understood that also the outer surface 11 of the complimentary wall portion 7, the other wall portions 20 and other parts of the stent are provided with micro-incisions 12. The micro incisions have a width, length and depth of 0.2 mm to 1 mm. The micro-incisions 12 provide a suction effect when the outer surface 10 is in contact with a duct wall. The suction effect enhances the force of pressing the stent-valve and the duct wall together, therefore enhancing also the friction force.

Figure 3:
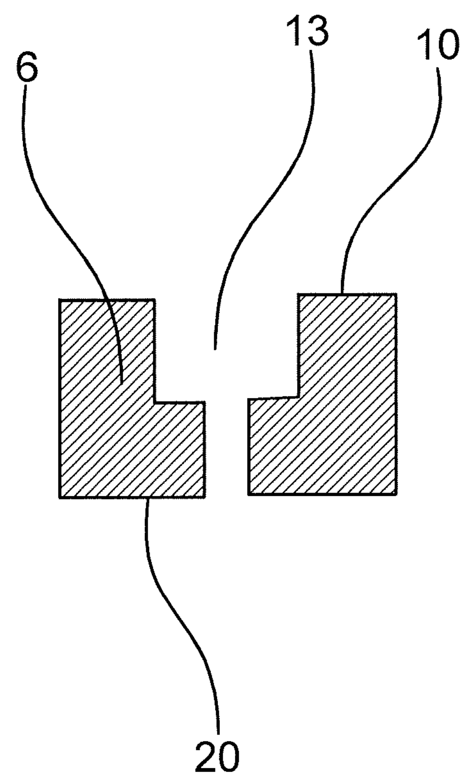

FIG. 3 shows a strut of an alternative support wall portion 6. The micro-incision is designed as a pass through micro-incision 13 from the outer surface 10 to an inner surface 20. Also the micro-incision 13 is provided by laser-cutting. The micro-incision 13 allows a deep tissue ingrowth and is arranged on the whole outer surface 10 and also on the outer surface 11 of the complementary wall portion 7. The pass through micro-incision is in a stepped form, having a larger diameter on the outer surface than on the inner surface of the strut.

As noted further above (in the paragraph beginning "It is of course possible"), the pass through orifices (micro-incisions) can be combined with other COF enhancing structures on the outer surface. In other words, a combination of pass through orifices (for example, the pass through micro-incision 13 shown in Figure 3) and non-pass through incisions (for example, the non-pass through micro-incision 12 shown in Figure 2) or with protrusions is possible.

FIGS. 4*a*-4*d* show different forms of micro incisions 12. FIG. 4*a*, shows a combination of two micro-incision forms 12. One micro incision is in the form of a double V-form 14, the other in a double line form 15, whereas the lines are perpendicular to a flow direction. FIG. 4*b* shows an X-form 16 and a double X-form 17. FIG. 4*c* shows a double rectangular-form 18 and FIG. 4*d* shows a triangle-form 19. A combination of the different micro-incision forms is of course possible. It is also in the sense of the invention that the micro-incisions can be constructed as pass through micro-incisions, passing through from the outer surface 10, 11 to the inner surface 20 of the stent 1.

Figure 5:
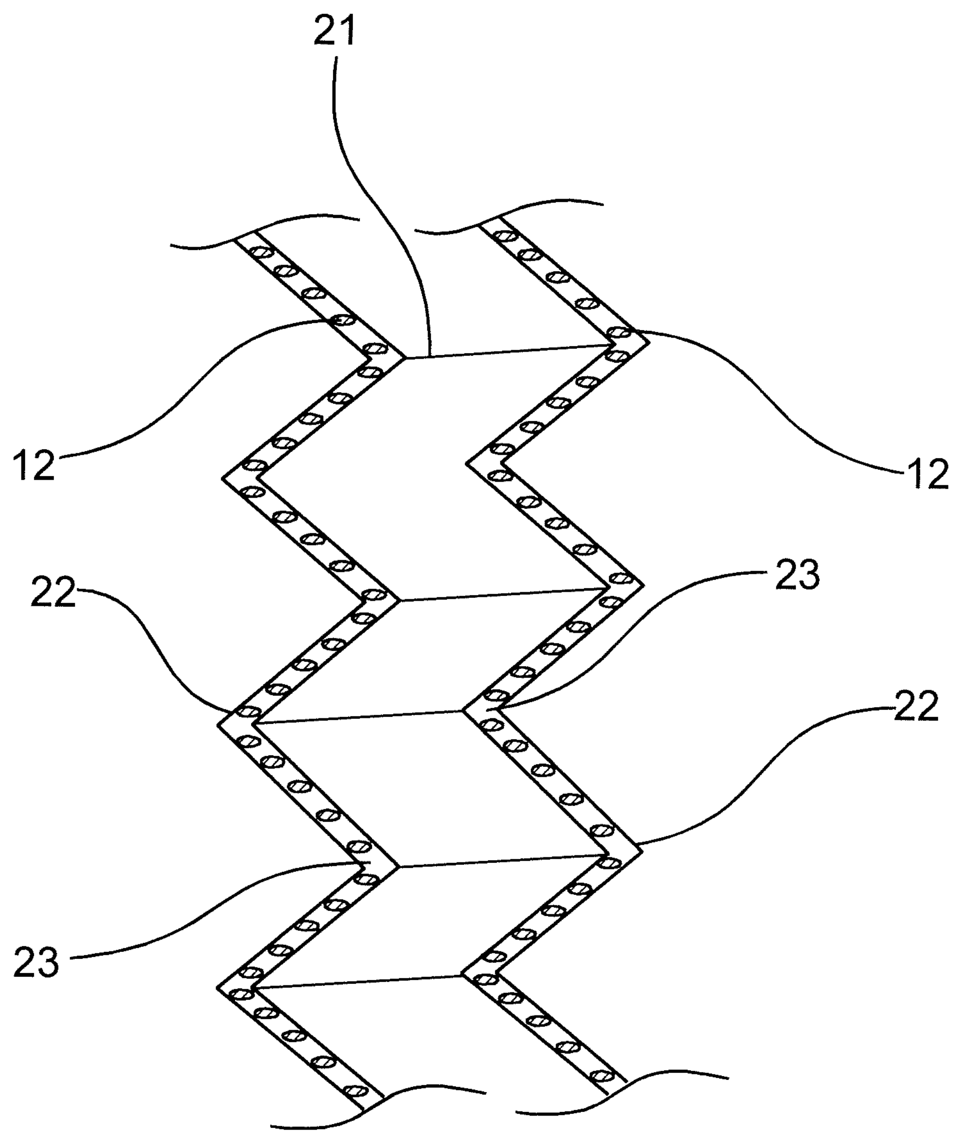

FIG. 5 shows a detailed view of two structured wall portions 20. The wall portions 20 are linked together with linker portions 21. The linker portions itself can be provided with micro-incisions (not shown in FIG. 5). The wall portions 22 are each provided with annular micro-incisions 12 on their outer surfaces 23. Multiple wall portions 22 together, form a generally tubular stent, when linked with linker portions 21.

The invention claimed is:

1. An expandable cardiac stent-valve comprising:

a stent component, and a cardiac valve component, wherein the stent component includes struts that have an outer surface area comprising structures to form a treated outer surface area, wherein the treated outer surface area has a higher coefficient of friction between the struts and a duct wall of a human than an untreated outer surface area of the stent component, wherein the structures of the treated outer surface area include at least one of a line form, V-form, double V-form, X-form, double X-form, a rectangular-form, a double rectangular-form, a triangle-form, and a double-triangle-form, wherein the structures comprise pass through micro-incisions that pass through from the outer surface area to an inner surface of the struts; and wherein the pass through micro-incisions have a larger opening on the outer surface area of the struts than on the inner surface of the struts.

2. The cFardiac stent-valve according to claim 1, wherein the structures of the treated outer surface area are created by laser cutting and/or chemical hatching and/or mechanical tooling.

3. The cardiac stent-valve according to claim 1, wherein the expandable cardiac stent-valve operates as a mitral stent-valve, a tricuspid stent-valve, an aortic stent-valve, or a pulmonary stent-valve.

4. The cardFiac stent-valve according to claim 1, wherein the structures provide a suction effect when the treated outer surface area is in contact with the duct wall.

5. The cardiac stent-valve according to claim 1, wherein the structures include the line form, the line form including a plurality of lines that are perpendicular to a flow direction.

6. The cardiac stent-valve according to claim 1, wherein the pass through micro-incisions have a stepped form in a longitudinal direction from the outer surface area of the struts to the inner surface of the struts.

* * * * *